(12) United States Patent
Bracht et al.

(10) Patent No.: US 8,226,974 B2
(45) Date of Patent: Jul. 24, 2012

(54) HIGHLY FLEXIBLE TRANSDERMAL THERAPEUTIC SYSTEM HAVING NICOTINE AS ACTIVE SUBSTANCE

(75) Inventors: Stefan Bracht, Ochtendung (DE); Sabine Warnus, Ettringen (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 1165 days.

(21) Appl. No.: 10/469,163

(22) PCT Filed: Feb. 19, 2002

(86) PCT No.: PCT/EP02/01728
§ 371 (c)(1), (2), (4) Date: Aug. 27, 2003

(87) PCT Pub. No.: WO02/069940
PCT Pub. Date: Sep. 12, 2002

(65) Prior Publication Data
US 2004/0096490 A1 May 20, 2004

(30) Foreign Application Priority Data
Mar. 3, 2001 (DE) .................................. 101 10 391

(51) Int. Cl.
*A61F 13/02* (2006.01)
*A61F 13/00* (2006.01)
*A61L 15/16* (2006.01)
*A61K 9/70* (2006.01)

(52) U.S. Cl. .................... 424/448; 424/449; 424/443
(58) Field of Classification Search .................. 424/449, 424/448, 443
See application file for complete search history.

(56) References Cited

U.S. PATENT DOCUMENTS

| | | | | |
|---|---|---|---|---|
| 4,915,950 | A | * | 4/1990 | Miranda et al. ............... 424/448 |
| 5,110,599 | A | * | 5/1992 | Anhauser et al. ............. 424/449 |
| 5,176,915 | A | | 1/1993 | Hoffmann |
| 5,364,630 | A | | 11/1994 | Osborne et al. |
| 5,456,745 | A | | 10/1995 | Roreger et al. |
| 5,603,947 | A | | 2/1997 | Wong et al. ................... 424/448 |
| 5,626,866 | A | | 5/1997 | Ebert et al. |
| 6,139,868 | A | | 10/2000 | Hoffmann ..................... 424/449 |
| 6,190,689 | B1 | | 2/2001 | Hoffmann et al. |

FOREIGN PATENT DOCUMENTS

| | | |
|---|---|---|
| CA | 2370019 A1 * | 11/2000 |
| DE | 43 32 094 A1 | 3/1995 |
| DE | 196 53 605 A1 | 6/1998 |

(Continued)

OTHER PUBLICATIONS

Polymethacrylate, "Handbook of Pharmaceutical Excipients", Arther H. Kibbe, 3rd ed., pp. 401-406 (2000).*

(Continued)

*Primary Examiner* — Isis Ghali
(74) *Attorney, Agent, or Firm* — ProPat, L.L.C.

(57) ABSTRACT

The invention relates to transdermal therapeutic systems which have the active ingredient nicotine and have particularly high flexibility. This flexibility decisively improves wearer comfort on the skin, since the system is readily capable of adapting to the surface of the skin and its constant movement. Surprisingly, the nicotine TTS of the invention is markedly more flexible than the conventional nicotine TTS products which are leaders in the market, although at least some of those systems are comparably thin.

15 Claims, 2 Drawing Sheets

FOREIGN PATENT DOCUMENTS

| | | |
|---|---|---|
| DE | 196 53 606 A1 | 6/1998 |
| DE | 198 26 592 A1 | 12/1999 |
| DE | 199 18 106 A1 | 10/2000 |
| EP | 0 303 025 B1 | 2/1989 |
| EP | 366 240 A1 | 5/1990 |
| EP | 0 484 543 A1 | 5/1992 |
| EP | 0484543 A1 | 5/1992 |
| EP | 708 627 A1 | 1/1995 |
| EP | 720 474 A1 | 3/1995 |
| EP | 0 916 339 A1 | 6/1999 |
| JP | 61251619 A | 11/1986 |
| KR | 1993-21198 | 6/1993 |
| WO | WO 88/01516 A1 | 3/1988 |
| WO | WO 94/04109 A1 | 3/1994 |
| WO | WO 95/24172 A1 | 9/1995 |
| WO | WO 00/33812 A1 | 6/2000 |
| WO | WO 00/64418 A2 | 11/2000 |

OTHER PUBLICATIONS

Hawlwy's Condensed Chemical discionary, Fourteenth Edition., p. 785.*
(Cf. M. Th. Schuler in Kunststoffe-Plastics, Sep. 1974, pp. 13-20.
Venkatraman S et al. "Skin adhesives and skin adhesion—1. Transdermal drug delivery systems" Biomaterials, Elsevier Science Publishers BV., Barking, GB Bd. 19, Nr. 13, Jun. 1998 pp. 1119-1136.

* cited by examiner

HIGHLY FLEXIBLE TRANSDERMAL THERAPEUTIC SYSTEM HAVING NICOTINE AS ACTIVE SUBSTANCE

BACKGROUND OF THE INVENTION

Prior Art

Transdermal therapeutic systems (TTSs) comprising nicotine have been described in the market and also in many patent specifications. Examples which may be mentioned are: EP-A 708 627, EP-A 366 240, EP-A 720 474, U.S. Pat. No. 5,364,630, WO 95/24172, WO 94/04109, WO 00/33812, WO 88/01516. Reference is also made to the current TTS products which are market leaders: NICOTINELL® TTS HABITROL® TTS in the US), NICORETTE® TTS (NICOTROL® TTS in the US) and NICODERM® TTS.

There are two problem areas substantially determining how nicotine TTSs are developed:
1. Nicotine is very volatile. Preparation processes which encompass drying steps are therefore made difficult or impossible.
2. Nicotine is a powerful plasticizer or solvent for polymers and plastic films as typically used in the production of TTSs.

The problems in 1. have led to the development of processes in which there is no need to dry the nicotine-containing material, and there is therefore no escape of nicotine through evaporation or vaporization.

The problems in 2. have led to many descriptions of polymers and plastic films which are particularly resistant to nicotine. This applies not only to pressure-sensitive-adhesive formulations but also to the protective and backing layers of TTSs, and also to suitable primary packaging.

All of the solutions found to these problems have hitherto been associated with some compromises with regard to complex system structure, and also in particular with regard to the thickness of the TTSs, which is sometimes considerable.

To avoid coating and drying, processes have been described for printing part or all of the surface of TTSs or individual layers thereof, but these require the presence of absorbent webs or papers. Nicotine can also be fed in liquid or thickened form into a reservoir system. However, systems of this type require considerable resources for production and are often thick and have a less than attractive appearance. Hot-melt processes may also be used, avoiding the use of solvents and making drying unnecessary. However, these imply, inter alia, considerable limitations in the selection of the polymers and auxiliaries. The plasticizing properties of nicotine have proven to be particularly problematic for the use of pressure-sensitive acrylate adhesives, since these have a relatively low glass transition temperature even when pure, this being the basis for their high spontaneous adhesion to human skin. Even with low concentrations of nicotine, therefore, a critical soft consistency arises and results in streaking and stringing, and very generally to problems with handling of the adhesive films, either on machines or manually.

For this reason, the systems proposed hitherto in connection with pressure-sensitive acrylate adhesives have almost exclusively had a particularly thick multilayer structure, each being required to absorb only a relatively low concentration of nicotine. Although the acrylate group also permits the selection of relatively high-molecular-weight products whose greater molecular weight gives them greater resistance to plasticizing substances such as nicotine, these can only be processed by the hot-melt process, and the selection of acrylates of this type available specifically for pharmaceutical applications rather than solvent-based pressure-sensitive adhesives is very restricted. In this context, there have hitherto been many systems proposed based on other polymers less sensitive to nicotine, e.g. hydrocarbon polymers, such as polyisobutylene or polybutylene, or else block copolymers of styrene with isoprene or butadiene. Silicone polymers have also been proposed, but of all the polymers available these are easily the most expensive. Finally, the systems marketed have marked differences in size for the same dispensing rate, this again being the result of the different resistances of the systems to the amount of nicotine present.

A general rule is that nicotine-resistant polymers have relatively high molecular weight and/or should have a glass transition temperature which is relatively high for pressure-sensitive adhesives. Among the polymers commonly used for producing TTSs, this consideration is least applicable to pressure-sensitive acrylate adhesives which can be processed using solvents.

In summary, it may be said that when compared with conventional matrix systems with other active ingredients (e.g. estrogen), the nicotine TTSs currently marketed are of unusually thick and stiff design, for the abovementioned reasons. With system areas of from 20 to 30 cm$^2$, this considerably reduces wearer comfort.

The object of the present invention was to provide a thin and highly flexible nicotine TTS which has considerably better wearability than conventional nicotine TTSs. The structure of the system should moreover be very simple, and it should be possible to use a solvent-containing coating for its production.

BRIEF DESCRIPTION OF THE INVENTION

The invention achieves this object by means of a transdermal therapeutic system which comprises nicotine and, where appropriate, other active ingredients and/or auxiliaries which act on the central nervous system, and is composed of a backing layer (1) impermeable to nicotine and to the other active ingredients and auxiliaries, and preferably also to water vapor, of a nicotine-containing intermediate matrix layer (2) immediately adjacent to the backing layer, of another nicotine-containing matrix layer (3), and of a peelable protective film (4), wherein all of the matrix layers are composed of (meth)acrylate copolymers which can be processed in solvent-containing systems, and where the total thickness of these layers (i.e. only the matrix layers together with the backing layer, i.e. excluding the protective film (4)) does not exceed 250 µm. The (meth)acrylate copolymers used in the transdermal therapeutic systems of the invention are therefore exclusively those capable of being processed in solvent-containing systems, and there is no need for any strengthening layers made from foreign polymers, or for reinforcement, such as paper or nonwoven.

DETAILED DESCRIPTION OF THE INVENTION

Figure 1A:
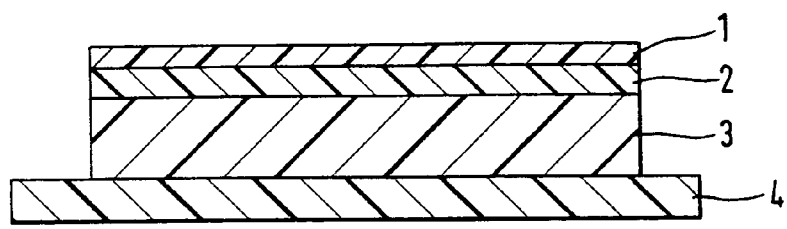
FIG. 1A is a cross-sectional schematic illustration of a typical inventive transdermal therapeutic system.

The term (meth)acrylate copolymers used here means copolymers made from acrylates and/or from methacrylates, i.e. alkyl esters whose alkyl radical advantageously has from 1 to 8, preferably from 1 to 6, in particular from 1 to 4, carbon atoms. Copolymers of this type may also be prepared with concomitant use of vinyl acetate, acrylic acid, and/or methacrylic acid. The property "capable of being processed in solvent-containing systems" implies that the (meth)acrylate copolymers have sufficient solubility or swellability in organic solvents to permit them to be cast without difficulty: (Meth)acrylate copolymers which have this capability are preferably those whose molecular weight is not above about 400 kDa. It is impossible to allocate a strict limit here, since the solubility of (meth)acrylate copolymers can be affected by adding certain auxiliaries, for example.

The nicotine loading of the transdermal therapeutic system is advantageously such that it comprises at least 1.5 mg of nicotine per cm$^2$ of application surface. The design of one advantageous embodiment of the system is such that from 0.7 to 1.4 mg, preferably from 1.0 to 1.4 mg, of nicotine is dispensed per cm$^2$ of skin within 24 hours, preferably within 16 hours.

The nicotine-containing intermediate matrix layer (2) is advantageously based on a polymer from the group of (meth)acrylate copolymers, preferably butyl methacrylate-(2-dimethylaminoethyl methacrylate)-methyl methacrylate copolymer, in particular a copolymer of this type having the molar ratio 1:2:1, or else a butyl methacrylate-methyl methacrylate copolymer.

The nicotine-containing matrix layer (3) is the pressure-sensitive-adhesive layer (adhesive layer) on the side facing the skin. This preferably has a structure based on acrylate copolymers which retain unesterified carboxy groups deriving from the acrylic or methacrylic acid and which have an acid value of from 20 to 100 mg KOH per g of polymer, for example, and which may have been neutralized completely or partially by one or more basic additives. Copolymers of this type are particularly plasticizer-resistant and, if they have been—preferably partially—neutralized, have very good nicotine-release properties. The design of these transdermal therapeutic systems can be surprisingly thin, and the systems have astoundingly high flexibility, even when compared with competitive products which are similarly thin. Surprisingly, the invention permits the unprecedented production of nicotine TTSs which have this degree of thinness and are at the same time highly flexible, with flexural stiffness of not more than 2 cN×cm$^2$.

Examples of additives which are used with the acrylate copolymers containing carboxy groups are alkali metal hydroxides, preferably potassium hydroxide, and basic polymers, preferably the abovementioned butyl methacrylate-(2-dimethylaminoethyl methacrylate)-methyl methacrylate copolymer. In one particularly advantageous embodiment, the acrylate copolymer containing carboxyl groups has been crosslinked by aluminum ions or titanium ions.

It is advantageous for their also to be at least one strongly water-binding auxiliary present in the TTSs of the invention, preferably a polymer containing carboxy groups or its pharmaceutically acceptable salt. This is preferably an auxiliary from the group consisting of the sodium or calcium salts of crosslinked carboxymethylcellulose or of crosslinked polyacrylic acid, and it is advantageous for this auxiliary to be present in powder form, dispersed in one or more of the matrix layers. The content of the water-binding constituent in the matrix is generally from 1 to 10% (w/w), preferably from 2 to 4% (w/w).

The other active ingredients and/or auxiliaries which act on the central nervous system and may be used are those previously described in the prior art in connection with nicotine for transdermal therapeutic systems, e.g. agents with stabilizing action, such as conventional antioxidants, preferably Vitamin E or ascorbyl palmitate.

Flexibility means the capability of a sheet to bend and thus adapt to an uneven surface. In practically all regions of the body, the skin is an uneven surface, all the more so since movements of the body constantly change the shape of its surface. The method for, and result of, comparative flexibility tests are described at a later stage. These also clearly show that the low flexural stiffness of not more than 2 cN×cm$^2$ is not merely a function of low system thickness but is also a function of the particularly flexible layer structure and/or of the matrix formulation. A fact which is of assistance here is that the TTSs of the invention comprise no separate active ingredient depots and no reinforcement, and no control membranes.

Compared with products available in the market, this novel formulation is at least equivalent or even superior in dispensing rate from the nicotine TTS per unit of area and time. This is demonstrated by other comparative studies, also described at a later stage in this specification.

The use of nicotine and, where appropriate, liquid auxiliaries generally means high loading of the matrix layers with plasticizing constituents. The formulations used for the pressure-sensitive-adhesive matrix layer(s) are therefore particularly plasticizer-resistant. Examples of these are cationically crosslinkable acrylate copolymers. Partially neutralized acrylate copolymers containing carboxy groups, as described in DE-A 199 18 106, are particularly suitable.

FIG. 1A shows a typical system structure for a matrix TTS of the invention. A backing layer (1), preferably impermeable to water vapor, is followed by an intermediate matrix layer (2). There is then a pressure-sensitive-adhesive matrix layer (3). The pressure-sensitive-adhesive surface of (3) has been covered by a protective film (4), which is removed before the TTS is used.

Figure 1B:
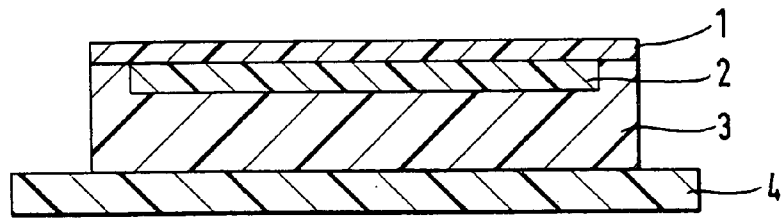
FIG. 1B is a cross-sectional schematic illustration of an alternative inventive transdermal therapeutic system embodiment.

Finally, depending on the production process, a system structure as in FIG. 1B may also be advisable. The intermediate matrix layer (2), not covering the entire surface, is introduced using printing technology, for example. The margin of the pressure-sensitive-adhesive matrix layer (3) is in direct contact with the backing layer (1), and the layer (3) therefore forms a final external margin around the inner intermediate matrix layer (2).

Polymers suitable for thickening the volatile constituent have been specified in DE-A 43 32 094. These are preferably not pressure-sensitive-adhesive polymers, since pressure-sensitive-adhesive polymers are practically impossible to obtain commercially free from solvent and are difficult to process in pure form.

Particularly suitable polymers for the present invention have proven to be those based on methacrylic acid or on its esters. Typical representatives of this group of polymers, such as EUDRAGIT® polymer grades, in particular EUDRAGIT® E polymer, or PLASTOID® B polymer, both products from Röhm GmbH, Darmstadt, Germany, have only modest thickening action in solution. This is desirable, since the initial polymer content of the solution can therefore be kept relatively high, generally from 20 to 40% (w/w). This permits rapid solidification of the solution to give a cohesive polymer film of adequate thickness and strength as equilibrium then becomes established. Polymethacrylates moreover have good anchoring properties on substrate webs made from polyethylene terephthalate (PET), these in turn being the preferred material for backing layers of TTSs.

Besides the polymer present, other auxiliaries may be added if required to reduce the content of active ingredient in the nicotine solution used. This can be advisable for adjustment of the amount of nicotine introduced into the system per unit area, or else to adjust to a suitable viscosity for coating with this solution. Additives of this type may also improve adhesion and, once the system has reached equilibrium, increase the bond strength between the separate layers in the composite. Without making any claim to completeness, some preferred additives are: triglycerides of saturated fatty acids (e.g. MIGLYOL® 812 a mixed acid triglyceride from fractionated coconut fatty acids from the company Degussa, Germany), monoglycerides of fatty acids (e.g, glycerol monolaurate or glycerol monooleate), esters of methanol, of ethanol, of isopropanol, or of propylene glycol with fatty acids (e.g, isopropyl palmitate), and also hard or soft resins in the form of derivatives of abietic acid.

Preferred suitable materials for the backing layer of the TTS are films with low nicotine permeability. Examples of these are polyethylene terephthalate, e.g. HOSTAPHAN® film from the company Mitsubishi (PET) and thermoplastic acrylonitrile copolymers, as obtained by graft polymerization of 73-77 parts of acrylonitrile and 23-27 parts of methyl acrylate in the presence of 8-18 of butadiene-acrylonitrile copolymer having 70% of butadiene (parts and percentages in each case being based on weight), marketed with the name BAREX® copolymer (previously: trademark of the company Vistron Corp., Cleveland, Ohio, USA; now BP). (Cf. M. Th. Schuler in Kunststoffe-Plastics, 9/1974, pp, 13-20). These films may have been provided with a surface finish for cosmetic reasons. If required, aluminum may have been applied to protect the nicotine-containing matrix layers from light.

Comparative Flexibility Tests

To allow objective assessment of this product quality feature, which is very easily perceived by the user, the DIN 53 362 method of determining flexural stiffness (cantilever method) for plastic films and sheet textiles was adapted, utilizing for this purpose test equipment complying with the standard and obtained from the company Richard Hess MBV GmbH, 47663 Sonsbeck, Germany. The principle here is that a specimen strip of the product to be tested is advanced by way of an edge freely into space. As the length of the overhang increases, the sheet bends downward under its own weight. The overhang length at which a prescribed angle of flex of 41° 30' is reached is recorded and converted by calculation into a value which measures flexural stiffness in the unit [cN×cm$^2$] as a function of the weight of the specimen.

The test specimens used were strips cut out from finished TTSs. The length of the test specimens here had to be restricted to the available length of the commercial products, deviating from the prescribed length of 250 mm in the DIN specification (the actual lengths of the test specimens being from 40 to 70 mm). The protective film for the adhesive layer was removed from the test specimens prior to the test. In accordance with the abovementioned DIN specification, the adhesive layer was covered with talcum powder until it was no longer tacky.

The test results (average from n=2 determinations) and the associated lengths of the test specimens are listed in table 1. The flexural stiffness of each test specimen was determined in both directions, i.e. with the backing layer upward for the first test and with the backing layer facing downward for the second test. This took account of the fact that a TTS should typically be flexible in both directions when worn on the skin. A novel nicotin TTS of the invention as in example 1 was compared with three marketed nicotine TTSs, and moreover with 2 marketed estradiol-containing products, which serve here as a useful reference for high flexibility and high wearer comfort.

TABLE 1

|  | Nicotine TTS A | Nicotine TTS B | Nicotine TTS C | Invention* | Estradiol TTS E | Estradiol TTS F |
|---|---|---|---|---|---|---|
| Flexural stiffness direction A | >14.5 cN × cm$^2$ | >8.9 cN × cm$^2$ | n.a. | 1.4 cN × cm$^2$ | 1.16 cN × cm$^2$ | 0.94 cN × cm$^2$ |
| Flexural stiffness direction B | >14.5 cN × cm$^2$ | >8.9 cN × cm$^2$ | 3.33 cN × cm$^2$ | 1.16 cN × cm$^2$ | 0.27 cN × cm$^2$ | 0.8 cN × cm$^2$ |
| System thickness without protective film | 238 µm | 389 µm | 394 µm | 218 µm | 110 µm | 117 µm |

*Nicotine TTS of the invention produced as in example 1 below.
n.a.: not applicable since test specimen formed a roll Nicotine TTS A refers to the product NICORETTE® TTS, a trademark of Pharmacia & Upjohn GmbH, Nicotine TTS B to NICODERM® CQ TTS, a trademark of SmithKline Beecham Consumer Healthcare L.P. (USA), Nicotine-TTS C to NICOTINE TRANSDERMAL USP TTS, marketed by Schein Pharmaceutical, Inc. (USA). Estradiol TTS E refers to DERMESTRIL® TTS, a trademark of the company Rottapharm s.r.l. (Monza, Italy), and Estradiol TTS F to Fem7®, a trademark of Merck KGaA, Darmstadt, Germany.

Direction A implies that the backing layer of the TTS is facing downward when the test specimen is tested, while the backing layer is upward for testing in direction B.

In some cases excessive stiffness meant that it was impossible to achieve the angle of flex of 41° 30' from the test specimens in the length available.

In those cases it was assumed that the result has to be greater than the value which would have been calculated if the critical angle had been reached using the overhang length possible with the test specimen.

In the case of nicotine TTS C, the product had a marked tendency to form a roll or to curl. This made it impossible to test in direction A. It was possible to utilize only the values measured in direction B.

The values measured show that the nicotine TTS of the invention has markedly lower flexural stiffness than the comparative TTSs using nicotine as active ingredient. Indeed, surprisingly, the values are in the region of those from two single-layer thin matrix TTSs with estradiol as active ingredient. These are among the most flexible TTSs in the current market.

Surprisingly, the flexural stiffness of the nicotine TTS of the invention is also very markedly below that of nicotine TTS A. There is only insignificant difference between the thicknesses of the two systems (nicotine TTS A about 238 μm, nicotine TTS of the invention about 218 μm)

EXAMPLES

Example 1

DE-A 43 32 094 discloses products and processes which permit the introduction of volatile pharmaceutical active ingredients or auxiliaries into TTSs. To this end, the volatile constituent is thickened by dissolving a polymer and, where appropriate, other solid auxiliaries in the volatile constituent as solvent in such a way that this solution can be coated onto a substrate web (=process step 1). This coated product is then laminated to other separately produced layers of the TTS, and then the volatile substance can reach equilibrium in the entire system through diffusion (=process step 2). The layer which was previously liquid solidifies there by diffusion of the volatile constituent, which is the only solvent, into the other layers of the TTS.

The composition of the polymer solution for process step 1 is as in table 2. An application system is used to coat this over the surface of a film made from polyethylene terephthalate of thickness 19 μm, the weight per unit area used being 54 g/m². The coated product is immediately laminated, in process step 2, to a pressure-sensitive-adhesive layer of composition as shown in table 3 and of thickness 144 g/m². The resultant product is heated to 60° C. for 10 minutes and then wound up onto a roll. This product is further processed in a conventional manner, immediately or else after intermediate storage, by longitudinal cutting and stamping to give TTSs.

TABLE 2

| Description | Amount [%] | Function |
|---|---|---|
| Nicotine | 32.41 | Volatile active ingredient |
| EUDRAGIT ® EPO | 27.00 | Methacrylate copolymer thickener |
| MIGLYOL ® 812 | 40.23 | Auxiliary |
| Vitamin E | 0.36 | Antioxidant |

TABLE 3

| Description | Amount [%] | Function |
|---|---|---|
| DUROTAK ® 387-2051 | 95.18 | Pressure-sensitive acrylate copolymer adhesive |
| KOH | 0.77 | Neutralizing reagent |
| Aluminum* | 0.05 | Crosslinking reagent for DUROTAK ® |
| Sodium salt of crosslinked carboxymethylcellulose | 4.00 | Hydroadsorbent |

*The aluminum is used in the form of Al acetylacetonate.

The adhesive layer as in Table 5 is produced by a conventional coating process in a solvent-containing system, followed by drying. The solvent used was a mixture of ethyl acetate, methanol, and acetylacetone. The coating took place onto a siliconized protective film made from polyethylene terephthalate (100 μm HOSTAPHAN® film).

The resultant TTS has about 1.75 mg of nicotine active ingredient content per cm² of application surface. This corresponds very closely to the content in nicotine TTS D. However, the thickness of the system of the invention is only about 218 μm (determined without protective film) and is therefore below that of the abovementioned systems.

Comparative Pharmacokinetic Studies

Figure 2:
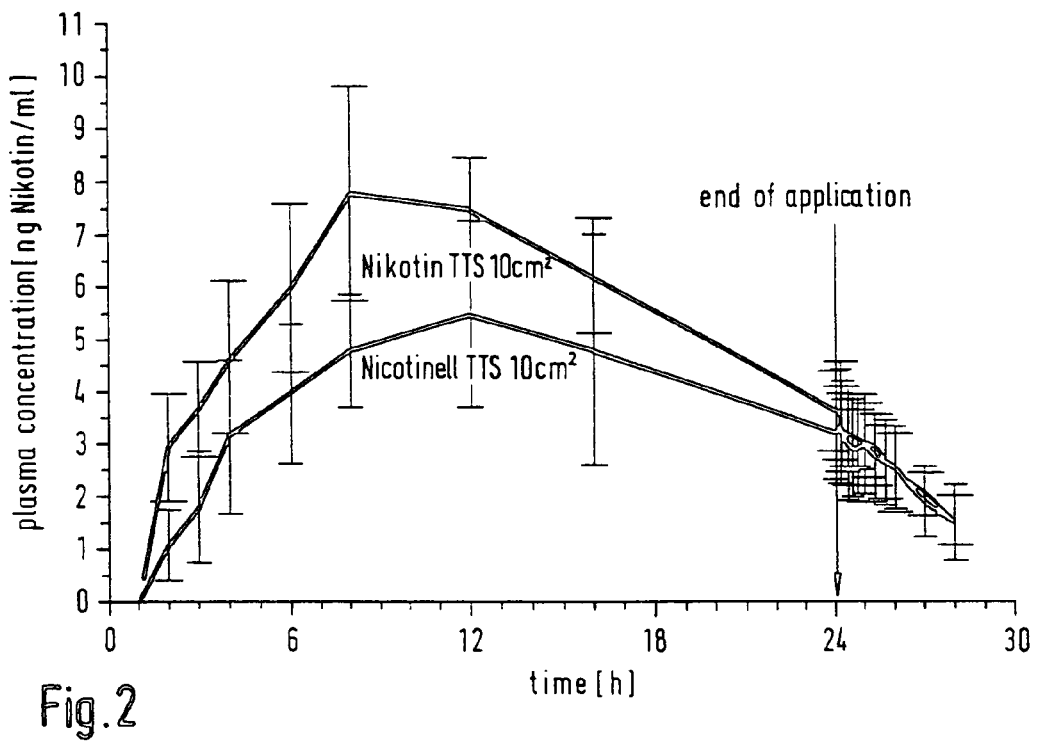
FIG. 2 is a graphical illustration of Plasma Concentration versus Time for two transdermal therapeutic systems.

The inventive nicotine TTS of example 1 was compared with a nicotine TTS D (NICOTINELL® TTS from Novartis Consumer Health Care S.A., Basle, Switzerland) in a pharmacokinetic study on humans (6 healthy male subjects using the inventive and the comparative preparation in succession—crossover design). The areas under the plasma level curve in FIG. 2 demonstrate superiority of the inventive nicotine TTS of the order of 140%, based on TTSs of identical area. This corresponds to a dispensing rate of about 1 mg of nicotine per cm² in 24 hours, whereas the value declared for nicotine TTS D is 0.7 mg per cm² in 24 hours.

Figure 3:
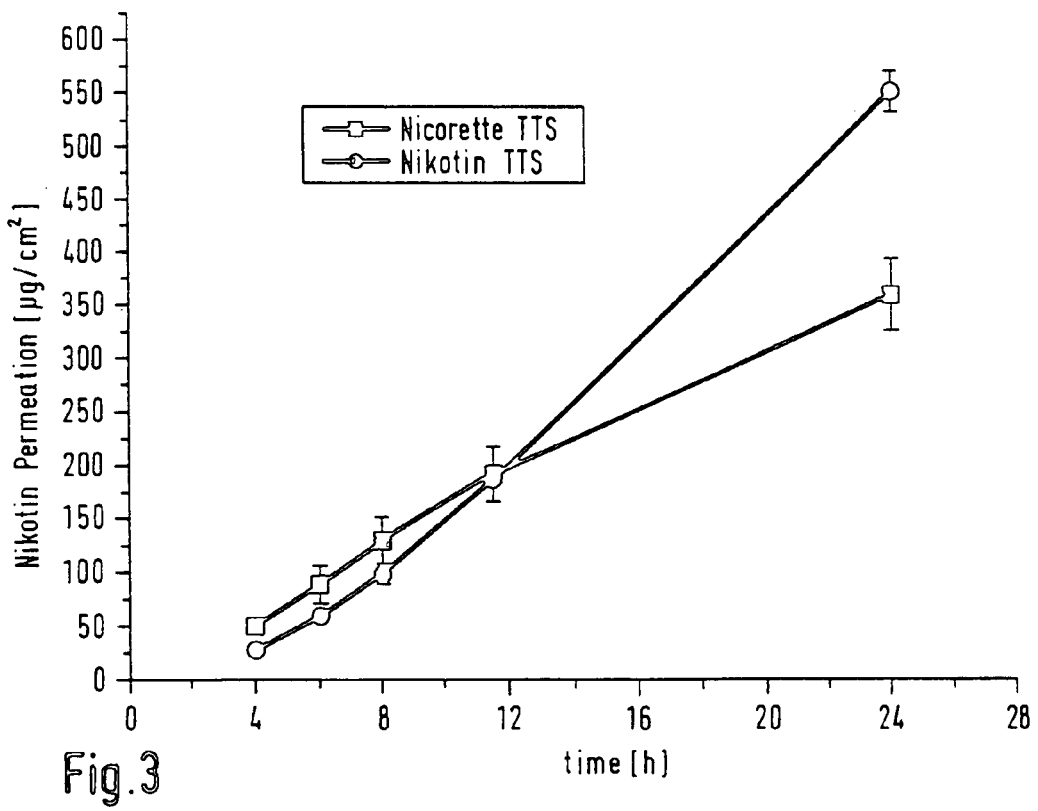
FIG. 3 is a graphical illustration of Permeation versus Time for two transdermal therapeutic systems.

A comparison was also made in vitro with nicotine TTS A. Permeation rates were determined on human skin in modified Franz diffusion cells commonly used for this purpose. The test temperature was 32° C., and an aqueous buffer of pH 5.5 was used as acceptor medium. All of the data are average values from n=3 specimens of skin from the same donor, determined using stamped TTS sections of area 1.12 cm². The results presented in FIG. 3 show the superiority of the inventive nicotine TTS over nicotine TTS A with respect to the total amount of nicotine dispensed per cm² in 24 hours.

Example 2

EP-B 0 303025 discloses a printing process with which nicotine can be introduced into each TTS. With the aid of this principle and printing equipment from the company Tampoprint, round areas of the active ingredient solution as in table 4 were applied by direct printing over the surface of a pressure-sensitive-adhesive layer whose composition was as in table 5, printing about 25 mg of nicotine solution onto an area of about 6 cm² of adhesive. The weight per unit area for the pressure-sensitive-adhesive layer as in table 5 was 144 g/m².

After print-application, the printed adhesive layer was immediately covered with a backing layer made from polyethylene terephthalate (15 μm HOSTAPHAN®film), to which it was mechanically laminated. The printed areas were stamped out from this composite using a round stamping tool. The diameter selected here for the stamped section was greater by about 4 mm (corresponding to about 8 cm² in area) than the diameter of the printed area. A system as in FIG. 1B was thus produced. On storage, nicotine equilibrium became established within all of the layers of the TTS.

TABLE 4

| Description | Amount [%] | Function |
|---|---|---|
| Nicotine | 60.00 | Volatile active ingredient |
| EUDRAGIT ® 100 | 40.00 | Methacrylate copolymer thickener |

TABLE 5

| Description | Amount [%] | Function |
|---|---|---|
| DUROTAK ® 387-2051 | 85.26 | Pressure-sensitive acrylate copolymer adhesive |
| KOH | 0.69 | Neutralization reagent |
| Aluminum* | 0.05 | Crosslinking reagent for DUROTAK ® |
| Sodium salt of crosslinked carboxymethylcellulose | 4.00 | Hydroadsorbent |
| EUDRAGIT ® E 100 | 10.00 | Basic auxiliary |

*The aluminum was added in the form of Al acetylacetonate.

The adhesive layer as in Table 5 is produced by a conventional coating process in a solvent-containing system, followed by drying. The solvent used was a mixture of ethyl acetate, methanol, and acetylacetone. The coating took place onto a siliconized protective film made from polyethylene terephthalate (100 µm HOSTAPHAN® film).

The invention claimed is:

1. A method for the manufacture of a transdermal therapeutic system with nicotine content, said system comprising
a backing layer impermeable to nicotine,
a first matrix layer immediately adjacent to the backing layer,
a second matrix layer, and
a peelable protective layer adjacent to the second matrix layer,
the total thickness of the backing layer and first and second matrix layers does not exceed 250 µm and the nicotine-content is at least 1.5 mg per $cm^2$ of application surface,
said method comprising
coating the second matrix layer onto the peelable protective layer,
applying the first matrix layer to a portion of the second matrix layer using printing technology,
said second matrix layer forming an external margin around the first intermediate matrix layer,
mechanically laminating the backing layer onto the applied first matrix layer and the external margin formed by the second matrix layer, and
establishing nicotine equilibrium within the layers,
wherein the matrix layers do not include non-woven;
the first matrix layer consists of (i) 60 to 80% (w/w) nicotine and (ii) a methacrylate copolymer thickener,
the second matrix layer as-applied consists of (i) (meth)acrylate copolymer adhesive consisting entirely of crosslinkable acrylate copolymers having an acid value of from 20 to 100 mg KOH per gram of polymer, (ii) crosslinker, (iii) a neutralization reagent, (iv) hydroabsorbent, and (v) methacrylate copolymer thickener.

2. A method as claimed in claim 1, wherein the flexural stiffness of the transdermal system to be applied to the skin is not more than 2 cN×$cm^2$.

3. A method as claimed in claim 1, wherein the matrix layers are free from supports and strengthening layers.

4. A method as claimed in claim 1, wherein the method further comprises the transdermal system dispensing from about 0.7 to about 1.4 mg of nicotine per $cm^2$ of skin within 24 hours.

5. A method as claimed in claim 4, wherein the method further comprises the transdermal system dispensing from about 1.0 to about 1.4 mg of nicotine per $cm^2$ of skin within 24 hours.

6. A method as claimed in claim 1, wherein the method further comprises the transdermal system dispensing from about 0.7 to about 1.4 mg, of nicotine per $cm^2$ of skin within 16 hours.

7. A method as claimed in claim 6, wherein the method further comprises the transdermal system dispensing from about 1.0 to about 1.4 mg of nicotine per $cm^2$ of skin within 16 hours.

8. A method as claimed in claim 1, wherein the methacrylate copolymer is a butyl methacrylate-(2-dimethylaminoethyl methacrylate)-methyl methacrylate copolymer or a butyl methacrylate-methyl methacrylate copolymer.

9. A method for the manufacture of a transdermal therapeutic system with nicotine content, composed of a backing layer impermeable to nicotine, a first matrix layer containing nicotine immediately adjacent to the backing layer, a second matrix layer, and a peelable protective layer, where the matrix layers are composed of (meth)acrylate copolymers, and the total thickness of the backing layer and first and second matrix layers does not exceed 250 µm and the nicotine-content is at least 1.5 mg per $cm^2$ of application surface,
said method comprising applying the first matrix layer using printing technology to a portion of the second matrix layer, said second matrix layer forming an external margin around the first matrix layer,
wherein the second matrix layer comprises a pressure-sensitive-adhesive based on acrylate copolymers and the acrylate copolymer of the second matrix layer contains carboxy groups and is completely or partially neutralized by one or more basic additives and/or in a form crosslinked by aluminum ions or titanium ions, and the basic additive is an alkali metal hydroxide or a basic polymer and
the first matrix layer consists of 60 to 80% (w/w) nicotine and polymer derived from methacrylic acid or esters thereof.

10. A method as claimed in claim 9, wherein the alkali metal hydroxide is potassium hydroxide and the basic polymer is butyl methacrylate-(2-dimethylaminoethyl methacrylate)-methyl methacrylate copolymer (1:2:1).

11. A method as claimed in claim 9, wherein at least one strongly water-binding auxilary is present in the second matrix layer of the transdermal system.

12. A method as claimed in claim 11, wherein the auxilary is a polymer containing carboxy groups or its pharmaceutically acceptable salt.

13. A method as claimed in claim 1, wherein the (meth)acrylate copolymers of the matrix layers are processed in solvent-containing systems.

14. A method as claimed in claim 1, wherein the transdermal therapeutic system has four layers.

15. A method according to claim 1, wherein said system consists of
(i) a backing layer impermeable to nicotine, (ii) a first matrix layer immediately adjacent to the backing layer, (iii) a second matrix layer, and (iv) a peelable protective layer adjacent to the second matrix layer,
and said method consists of
coating the second matrix layer onto the peelable protective layer,
applying the first matrix layer to a portion of the second matrix layer,
mechanically laminating the backing layer onto the applied first matrix layer and the external margin formed by the second matrix layer,
the first matrix layer consisting of nicotine and a methacrylate copolymer thickener,
the second matrix layer as-applied consisting of (i) (meth)acrylate copolymer adhesive consisting entirely of crosslinkable acrylate copolymers having an acid value of from 20 to 100 mg KOH per gram of polymer, (ii) crosslinker, (iii) a neutralization reagent, (iv) hydroabsorbent, and (v) methacrylate copolymer thickener.

* * * * *

UNITED STATES PATENT AND TRADEMARK OFFICE
CERTIFICATE OF CORRECTION

PATENT NO.          : 8,226,974 B2                                              Page 1 of 1
APPLICATION NO.     : 10/469163
DATED               : July 24, 2012
INVENTOR(S)         : Bracht et al.

It is certified that error appears in the above-identified patent and that said Letters Patent is hereby corrected as shown below:

Column 9

Claim 1, line 24, delete "intermediate"

Signed and Sealed this
Eleventh Day of September, 2012

David J. Kappos
*Director of the United States Patent and Trademark Office*